United States Patent
Vercruysse et al.

(10) Patent No.: US 8,640,557 B2
(45) Date of Patent: Feb. 4, 2014

(54) AUTOMATIC ANALYSIS OF FINELY DIVIDED SOLIDS

(75) Inventors: Karen Vercruysse, Melsele (BE); Frans Suykerbuyk, Wuustwezel (BE); Sven Veelaert, Ekeren (BE); Veron Nsunda, Namur (BE); Kris Wullus, Kruibeke (BE)

(73) Assignee: BASF SE, Ludwigshafen (DE)

( * ) Notice: Subject to any disclaimer, the term of this patent is extended or adjusted under 35 U.S.C. 154(b) by 187 days.

(21) Appl. No.: 13/318,802

(22) PCT Filed: May 11, 2010

(86) PCT No.: PCT/EP2010/056398
§ 371 (c)(1),
(2), (4) Date: Nov. 4, 2011

(87) PCT Pub. No.: WO2010/130703
PCT Pub. Date: Nov. 18, 2010

(65) Prior Publication Data
US 2012/0060592 A1   Mar. 15, 2012

(30) Foreign Application Priority Data
May 15, 2009 (EP) .................................. 09160425

(51) Int. Cl.
*G01N 1/00* (2006.01)
(52) U.S. Cl.
USPC ...................................................... 73/864.34
(58) Field of Classification Search
None
See application file for complete search history.

(56) References Cited

U.S. PATENT DOCUMENTS

| | | | |
|---|---|---|---|
| 2,777,324 A * | 1/1957 | Ives | ................................. 73/73 |
| 5,337,620 A | 8/1994 | Kalidini | |
| 5,440,941 A | 8/1995 | Kalidindi | |
| 5,492,023 A | 2/1996 | Kitamura et al. | |
| 5,599,335 A | 2/1997 | Goldman et al. | |

(Continued)

FOREIGN PATENT DOCUMENTS

| | | |
|---|---|---|
| DE | 35 32 786 | 5/1986 |
| JP | 58 206945 | 12/1983 |
| JP | 60 60532 | 4/1985 |

(Continued)

OTHER PUBLICATIONS

International Search Report Issued Apr. 20, 2011 in PCT/EP10/056398 Filed May 11, 2010.

*Primary Examiner* — Robert R Raevis
(74) *Attorney, Agent, or Firm* — Oblon, Spivak, McClelland, Maier & Neustadt, L.L.P.

(57) ABSTRACT

The present invention relates to a solids dosing device for finely divided solids, comprising sampling means for withdrawing a sample from a sampling jar and dosing means for inserting a prescribed amount of finely divided solid material into a testing jar, a dosing accuracy of at least 0.1 g being achieved with the solids dosing device and characteristics of the dosed amount substantially corresponding to those of the sample in the sampling jar. The invention also relates to an automated analyzer for determining properties of finely divided solids, comprising a depot for sampling jars and testing jars, analysis devices for the analysis of samples, manipulators for the movement and positioning of sampling jars, solids dosing devices and dosing devices for liquids. Furthermore, the invention relates to a method for the automatic analysis of finely divided solids.

14 Claims, 4 Drawing Sheets

(56) References Cited

U.S. PATENT DOCUMENTS

Figure 1A:
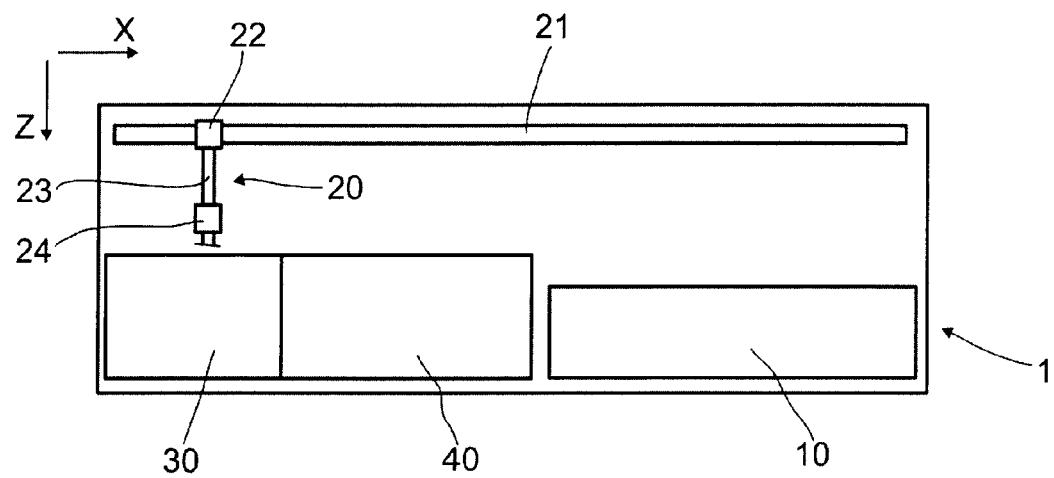

| | | | |
|---|---|---|---|
| 6,158,293 A * | 12/2000 | Poole | 73/866 |
| 6,339,966 B1 * | 1/2002 | Kalidindi | 73/864.31 |
| 6,631,650 B1 * | 10/2003 | Espinosa | 73/864.44 |
| 7,984,835 B2 * | 7/2011 | Fontaine et al. | 222/412 |
| 2005/0177134 A1 | 8/2005 | Gueller et al. | |
| 2007/0029342 A1 | 2/2007 | Cross et al. | |

FOREIGN PATENT DOCUMENTS

| | | |
|---|---|---|
| JP | 10 77121 | 3/1998 |
| WO | 93 15407 | 8/1993 |
| WO | 97 47974 | 12/1997 |

* cited by examiner

AUTOMATIC ANALYSIS OF FINELY DIVIDED SOLIDS

The present invention relates to a solids dosing device for finely divided solids, comprising sampling means for withdrawing a sample from a sampling jar and dosing means for inserting a prescribed amount of finely divided solid material into a testing jar. The invention also relates to an automated analyzer for determining properties of finely divided solids, comprising a depot for sampling jars and testing jars, analysis devices for the analysis of samples, manipulators for the movement and positioning of sampling jars, solids dosing devices and dosing devices for liquids. Furthermore, the invention relates to a method for the automatic analysis of finely divided solids.

Quite a lot of chemical processing products are in the form of solids or powders. Their effective properties often depend on physical properties such as the particle size or the grain size distribution. In order to ensure consistent quality, the solids or powders are analyzed at regular intervals. This often involves the use of methods of analysis that are specifically designed for the respective product and are carried out in a standardized procedure. The term analytics is to be understood hereafter in the sense that its objective is to obtain representative and comparable findings concerning properties of samples of solid materials.

In the following, no distinction is drawn between powders and solids in the form of free-flowing bulk materials, but instead both are covered by the term "finely divided solids". The particle sizes are in this case in a range from 1 to 1500 micrometers (μm).

An example of such products are water-absorbing polymers, which are also referred to as superabsorbers. They comprise hydrophilic polymers, which are so strongly crosslinked that they are no longer soluble. Their preparation is described, for example, in the monograph "Modern Superabsorbent Polymer Technology", F. L. Buchholz and A. T. Graham, Wiley-VCH, 1998, pages 71 to 103, and in Ullmann's Encyclopedia of Industrial Chemistry, 6th edition, volume 35, pages 73 to 93. Typical grain size distributions can be determined by screening analysis. In this case, 90%, 95% or 98% of the particles respectively lie in the range from 150 to 850 μm. Until now, the required analyses have mostly been carried out manually, which involves considerable expenditure in terms of work and time. It is known from other areas, for example the pharmaceuticals industry, to use automatic systems for carrying out standardized analyses.

For instance, WO 93/15407 describes a universal laboratory robot, in particular for use in the medical sector. Samples of substances are kept in jars in a store. According to a fixed sequence of steps, the robot transports the jars from the store to various analysis stations. There, the samples are automatically analyzed and subsequently taken back to the store by the robot.

WO 97/47974 discloses a laboratory robot for the analysis of liquid, solid or powdered samples. The laboratory is divided into what are referred to as a robot zone and an operator zone, which are separated from one another by a wall. With the aid of transporting belts, samples to be analyzed are exchanged between the zones. Various analysis stations in which the samples can be automatically analyzed are set up in the robot zone. An at least five-axis robot can be moved on a longitudinal rail, so that it can transport samples between various transporting belts and the analysis stations.

Apart from the automation of complete methods of analysis, solutions to partial problems are also known. JP 10077121 describes the dosing of finely divided solids into small amounts (1 to 5 mg), primarily for use in drug development. In this case, the respective sampling bottle is taken up by a robot, the lid is removed and the bottle is placed upside down on the dosing device. By turning a brush, the required amount of solid material is withdrawn from the sampling bottle and allowed to pour into the testing jar.

The invention described below was based on the object of providing an apparatus and a method for the automated analysis of finely divided solids, with the intention of ensuring that representative and comparative findings can be obtained with regard to the properties of the product. In this context, a further object is that of developing a dosing device for finely divided solids for use in said apparatus. To achieve this object, a solids dosing device as claimed in claim 1, an automated analyzer as claimed in claim 6 and a method as claimed in claim 8 or 9 are proposed. Specific refinements of the solution according to the invention are presented in the respectively dependent claims.

According to the invention, the solids dosing device comprises sampling means for withdrawing a sample from a sampling jar and dosing means for inserting a prescribed amount of finely divided solid material into a testing jar.

In order to analyze finely divided solids with regard to their characteristic properties, usually samples are taken, for example from the production process or from the sales product. The sample should be of a certain minimum amount in order to minimize random variations in the particle sizes and their distribution. With a particle size of 150 to 850 μm, a sample amount of 1000 $cm^3$ has proven to be favorable.

Sampling jars in which the sample is provided for analysis may take various forms. Apart from straight, tubular jars, jars in the form of bottles, in which the diameter narrows toward the opening, are also popular. The cross section may at the same time take various forms, such as circles, ovals, rectangles or hexagons, for example also with rounded corners. The sampling jars may also be closable, for example by closures that turn, tilt or snap. Closable sampling jars are used with preference if the properties of the finely divided solids to be analyzed may change as a result of contact with the atmosphere surrounding them, for example on account of the oxygen content or the moisture in the air.

The sample is often a mixture of many particles with different properties, such as size and shape. The properties of the mixture of interest is in turn dependent on the properties of the particles, and consequently on the composition of the mixture. It is therefore expedient to provide the most uniform possible mixing of the sample in the sampling jar and to counteract adverse effects such as segregation. This may take place manually or in an automated manner, for example by shaking or rotating the sampling jars or else by stirring in the sampling jar.

To carry out the individual analyses, partial amounts of the sample are required in testing jars. The size, form and nature of the testing jar is in this case depend on the method and the actual equipment of the analysis that is respectively to be carried out. Suitable testing jars may be, for example, beakers, dishes or measuring cells, which may be produced from glass, plastic, metal or other materials. The respectively required amounts of finely divided solids in the testing jars vary according to the substances to be analyzed and the methods of analysis. For water-absorbing polymers, for example, the required amounts in the testing jars lie in a range from 0.2 to 2.0 g.

According to the invention, representative partial amounts of the sample of finely divided solids are withdrawn from the sampling jars with the aid of sampling means. In this context, representative means that characteristics of the sample in the sampling jar, such as the grain size distribution, are also found in the partial amount withdrawn. Suitable sampling means are, for example, grippers, which are inserted into the sample in the open state, closed there and, in the closed state, withdraw a partial amount of the sample from the sampling jar. A preferred embodiment takes the form of a hollow lance, as explained by way of example below with reference to the drawings. It is advantageous if a sampling means displaces the smallest possible volume in the sampling jar or exerts only little pressure on the particles of the solid material, in order to avoid non-uniform distribution, compression or damaging of the particles of solid material to the greatest extent. This effect can be achieved, for example, by a small cross-sectional area or a shaping of the sampling means with which the diameter is reduced or forms a tip in the direction of the inserted end.

In order to insert the withdrawn partial amounts into testing jars, according to the invention dosing means are used. These may be conveying devices, for example, with which the withdrawn partial amount is fed onto a screw by way of a funnel. The dosed amount of finely divided solids that is inserted into the testing jar can in this case be influenced by means of the rotational speed of the screw. In a variant, the screw may be replaced by a conveyor belt, the circulating speed of which can be controlled. In a preferred embodiment, an essential element of the dosing means is a dosing wheel, which is explained in more detail with reference to the following drawings.

Depending on the requirements of the respective method of analysis, dosing means are to be designed in such a way that dosing accuracies of at least 0.1 g, 0.01 g or 0.001 g are ensured. Depending on the actual embodiment of the dosing means, various possibilities for influencing the dosing accuracy are obtained. With the conveying screw, for example, the pitch of the screw, its diameter and the minimum rotational speed that can be set can be chosen appropriately. If a conveyor belt is used, the dosing accuracy can be influenced, for example, by choosing the roughness of the belt, its width and loading height as well as the rotational speed.

The amount of finely dispersed solids to be dosed may be prescribed and monitored in various ways. One possibility is to prescribe the filling height in the testing jar and to check the amount actually dosed by measuring the filling level, for example by means of laser techniques or imaging methods. In an alternative embodiment, the mass of the dosed solid material is determined, for example by the testing jar being located on a weighing device during the dosing operation.

Apart from high accuracy of the dosed amount of solid material, uniform distribution of the sample in the testing jar is also important for some methods of analysis. A dosing means according to the invention therefore provides the possibility of inserting the dosed finely divided solid material into a testing jar in such a way that homogeneity is obtained with regard to the local distribution of the mixture of solid material and the distribution of the characteristics of the particles in the mixture. In one embodiment, this is ensured by providing a stirring device, which during the dosing operation mixes the particles of solid material dosed into the testing jar and after completion of the dosing operation smooths off the surface of the dosed amount of solid material. In a further embodiment, the testing jar is moved in one or more planes during the dosing operation.

According to the invention, an automated analyzer, which comprises a depot, analysis devices, manipulators, solids dosing devices and dosing devices for liquids, is used for determining properties of the finely divided solids. The solids dosing devices are preferably embodiments according to the invention.

The depot represents an interface between the automated analysis of the samples and the operator of the automated analyzer. On the one hand, it offers the operator the possibility of placing and removing sampling jars and testing jars. On the other hand, the corresponding jars may also be removed from the depot and placed in the depot by a manipulator of the automated device. Furthermore, a depot serves for storing sampling jars and testing jars, for example if a method of analysis is provided with a waiting time between the preparation for analysis and the evaluation of the results.

The automated analyzer comprises one or more analysis devices for the analysis of samples of finely divided solids. The actual configuration of the analysis devices is in this case dependent on the respective method of analysis. Examples of actual methods of analysis are given below for water-absorbing polymers.

In order to move sampling jars and testing jars from one place to another and position them within the automated analyzer, at least one programmable manipulator is provided. Its structural design and functionality are closely related to the spatial arrangement of the further component parts of the automated analyzer. In one embodiment, in which the depot, analysis devices and dosing devices are arranged substantially in one spatial plane, a manipulator that can be moved in three spatial directions (x, y, z) is suitable. Depending on requirements, the manipulator may also have additional axes of rotation, for example if it is necessary to turn the jar to carry out dosing or analysis.

In a further embodiment, the depot on the one hand and the dosing devices and analysis devices on the other hand are arranged in two different spatial planes. In this case, the manipulator may be advantageously arranged between the planes and can be moved about an axis of rotation, perpendicularly to the axis in a radial direction and parallel to the axis. Also in this embodiment, further axes of rotation may be provided, for example for the rotation of a gripper.

Apart from a manipulator, which provides the transport of the sampling jars and testing jars, further programmable manipulators may be provided in the automated analyzer, for example to allow sampling means and dosing means to be moved in relation to one another. It is often sufficient if such a manipulator can be moved in one spatial direction.

Some methods of analysis require that the finely divided solids are brought into contact with one or more liquids. According to the invention, the automated analyzer therefore comprises one or more dosing devices for liquids. In one embodiment, a prescribed amount of liquid is dosed into a testing jar. This may be performed by a weighing device registering the weight of the testing jar and a controller influencing the inflow of liquid on the basis of this information. As an alternative to weighing, a flow meter may be used to register the dosed amount. For some test methods, a specific filling level in a testing jar must be ensured. For this purpose, one embodiment according to the invention provides a dosing device which is based on the principle of communicating tubes. In a further embodiment, the filling level is registered by means of sensors and the dosing is influenced correspondingly, for example by means of a hose pump. On the one hand, the dosing devices for liquids may be fixed in place in the automated analyzer. In this case, a manipulator transports the testing jars to be filled to the dosing devices. On the other hand, a dosing device for liquids may also be provided in a manipulator, for example in the gripper, so that liquid dosing can be performed at various places in the automated analyzer. There may also be more than one dosing device for liquids.

As already mentioned above, it is important for some methods of analysis that the finely divided solids are uniformly distributed in a testing jar. It is therefore advantageous if the manipulators are programmed in such a way that their movements are not jerky or subject to excessive accelerations. The setting of suitable parameters may, for example, be performed in advance by simulation calculations or by tests during the operation of the manipulator concerned. Furthermore, it has proven to be advantageous to isolate the depot for sampling jars and testing jars in terms of vibration from the other elements of the automated analyzer, for example in that it is mounted on a separate foundation and has no solid connection with elements of the automated analyzer. As a result, adverse effects such as the segregation of the particles of solid material in the jars caused by vibrations during transport or storage are avoided, or at least reduced.

The automated analyzer is suitable in particular for carrying out standardized analyses of a large number of samples. The analysis results are preferably made available in such a form that they can be further processed electronically. Apart from an operator interface, for this purpose the automated analyzer may have, for example, interfaces with a laboratory data information system (LIMS, Laboratory Information Management System) or an Operating Data Information System (PIMS, Process Information Management System). In the LIMS or PIMS, data output by the automated analyzer in relation to the respective samples, for example amounts of dosed finely divided solids or liquids, filling levels, time periods, analysis results or status information, can be archived and further processed. The automated analyzer may have further interfaces, which allow it to be linked up to a higher-level automation system, for example to a process control system or a business management planning tool (ERP, Enterprise Resource Planning).

The automated analyzer according to the invention and the method according to the invention for the automatic analysis of finely divided solids can be used in various areas. They are advantageously used for the recurrent, routine analysis of a large number of samples, for example for quality control in continuous or discontinuous production processes.

The invention is further explained below with reference to the drawings, where the drawings are to be understood as basic representations. They do not constitute any restriction of the invention, for example with regard to dimensions or relative sizes.

Figure 1B:
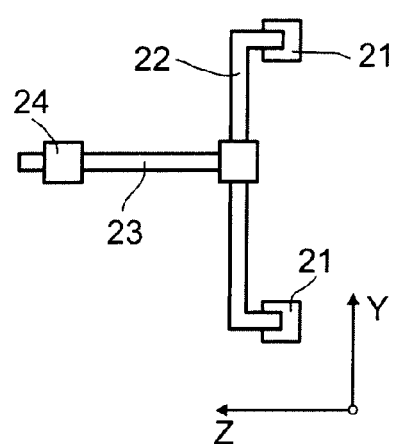
Figure 2A:
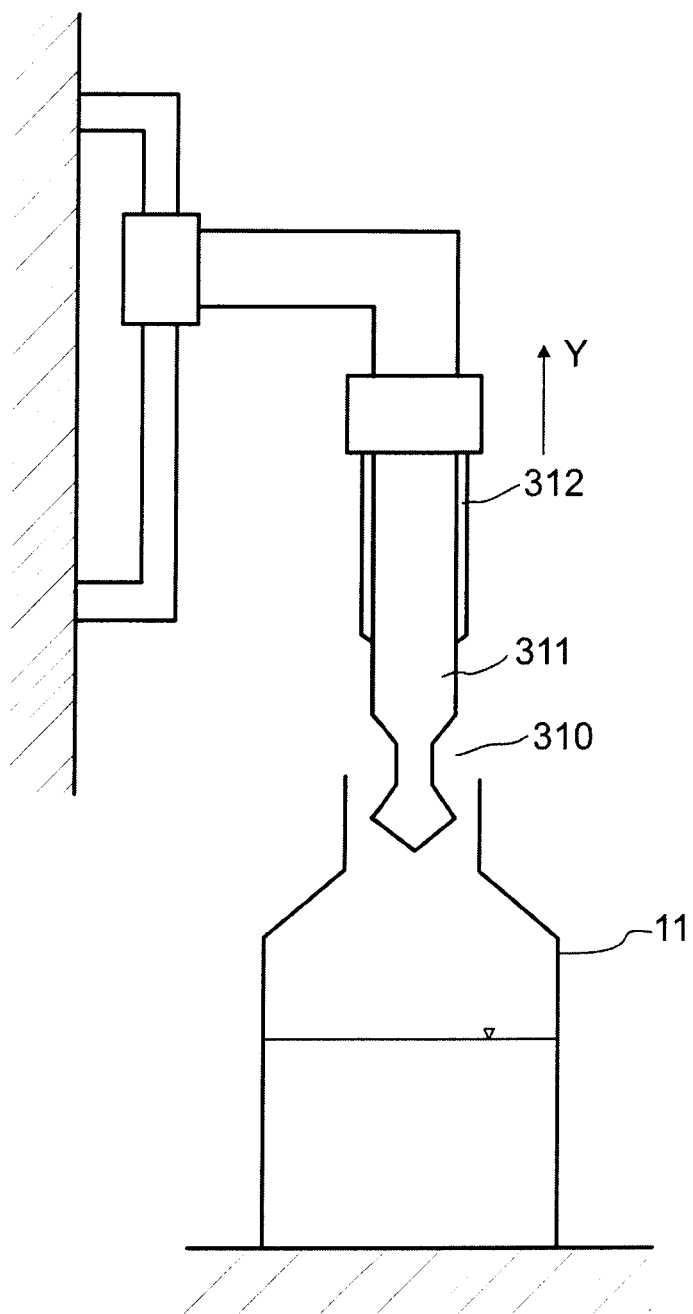
Figure 2B:
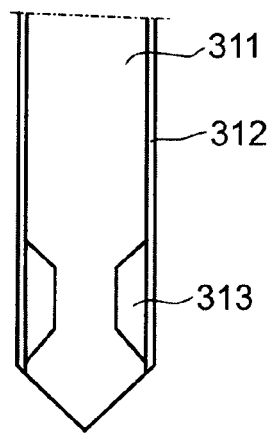
Figure 2C:
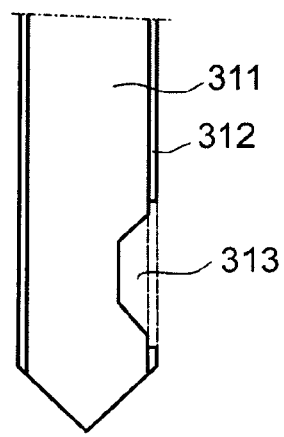
Figure 2C:
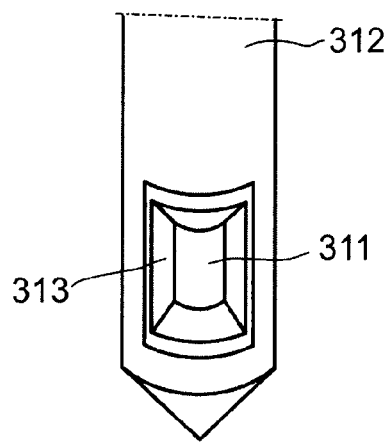
Figure 3:
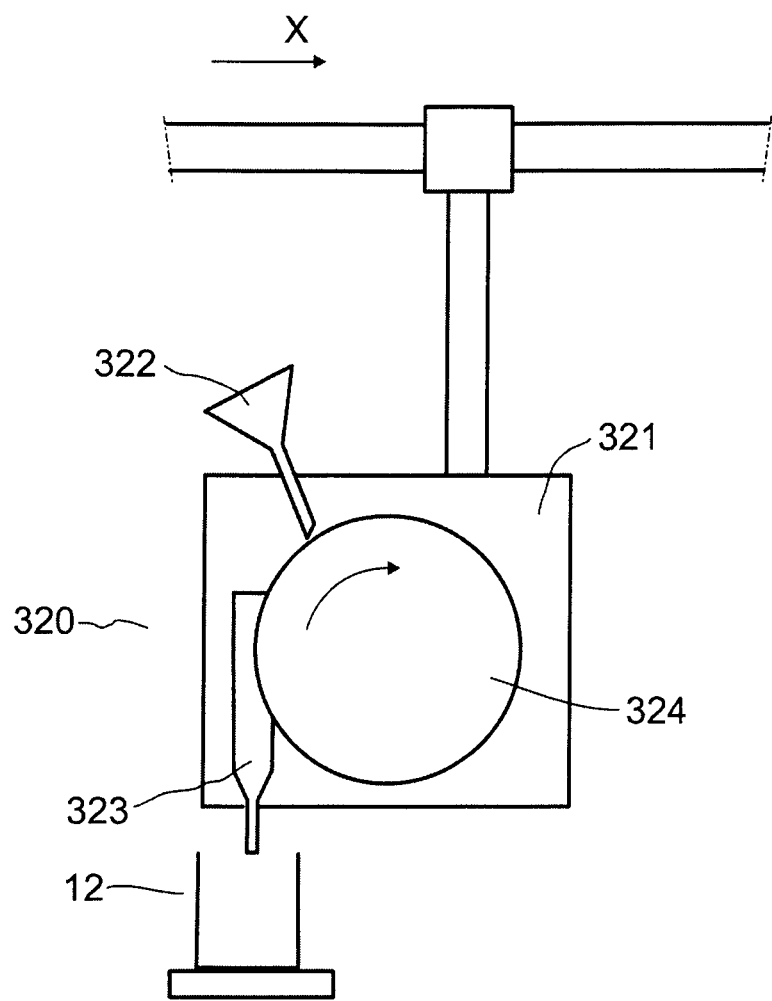

In the drawings:

FIG. 1a shows a plan view of an arrangement of an automated analyzer according to the invention FIG. 1b shows a view of a manipulator in an arrangement as shown in FIG. 1a FIG. 2a shows a basic diagram of a hollow lance as an embodiment according to the invention of a sampling means in the open state FIG. 2b shows a detail of a hollow lance as shown in FIG. 2a in the closed state FIG. 2c shows a basic diagram of an alternative embodiment of a sampling means in longitudinal section and in a perspective representation FIG. 3 shows a basic diagram of an embodiment according to the invention of a dosing means with a dosing wheel.

LIST OF DESIGNATIONS USED

1 . . . automated analyzer
10 . . . depot
11 . . . sampling jar
12 . . . testing jar
20 . . . manipulator
21 . . . guide rails
22 . . . manipulator carrier
23 . . . manipulator arm
24 . . . gripper
30 . . . dosing devices
40 . . . analysis devices
310 . . . hollow lance
311 . . . basic body
312 . . . sleeve
313 . . . sampling volume
320 . . . dosing means
321 . . . dosing means housing
322 . . . dosing means inlet
323 . . . dosing means outlet
324 . . . dosing wheel FIG. 1a shows a possible arrangement of an automated analyzer 1 according to the invention. The depot 10, dosing devices 30 and analysis devices 40 are located substantially in one plane. Provided opposite them is a manipulator 20, which can transport sampling jars and testing jars between the individual units. FIG. 1b schematically shows an embodiment of a manipulator 20 which can be moved in three axes. In order to be movable in the x direction, a manipulator carrier 22 is guided in guide rails 21, which are fastened for example to a wall of the automated analyzer 1. A manipulator arm 23 can be displaced along the manipulator carrier 22 in the y direction. The manipulator arm 23 and a gripper 24 located on it perform the movement in the z direction.

In FIG. 2a, a hollow lance 310 is schematically represented as an embodiment of a sampling means according to the invention. The sampling means is provided movably in the y direction, to allow it to be inserted into a sampling jar 11. This may be performed by the sampling means falling into the sampling jar 11 and being inserted into the solid material under the influence of gravitational force. The sampling means may, however, also be actively inserted into the sampling jar 11 by a drive.

In the example represented, the sampling means is formed as a hollow lance 310. In one embodiment, the hollow lance 310 comprises a basic body 311 of a substantially circular cross section. In the lower part, the diameter of the basic body 311 of the hollow lance is less over a certain length than in the upper part. The portion of reduced diameter is delimited in the downward direction by the diameter at the lower end of the basic body 311 again corresponding to at least the portion above the set-back portion.

The basic body 311 is enclosed by a sleeve 312, which is provided in such a way that it is movable in relation to the basic body 311. The sleeve 312 is designed such that it can be moved over the portion of the basic body 311 of reduced diameter. FIG. 2b shows the lower part of the hollow lance 310 as a detail in the closed state, in which the sleeve 312 completely encloses the portion of reduced diameter of the basic body 311. The closing operation in this case take place on the basis of gravitational force or else actively by a drive.

In order to withdraw finely divided solids from the sampling jar 11, the hollow lance 310 is inserted in the open state into the sample of solid material. It is also possible to insert the hollow lance in the closed state and only then open it. To ensure representative sampling, insertion depths of 40% to 80%, preferably 50% to 70%, of the filling height have proven to be advantageous, in each case with respect to the midpoint of the portion of reduced diameter of the basic body 311 and calculated from the surface of the filling of solid material. If the filling height in the sampling jar 11 is 10 cm, for example, the midpoint of the set-back portion should lie 4 to 8 cm, preferably 5 to 7 cm, below the surface of the filling. Even if inhomogeneities regarding the characteristics of the sample, for example the grain size distribution, occur, for example during the transport of the sampling jar 11, a sample that is as representative as possible is ensured by insertion into the region in the middle of the filling of solid material.

When the hollow lance 310 is inserted into the filling of solid material, the freely flowing nature of the finely divided solid material will cause it to arrange itself around the basic body 311. By means of the sleeve 312, a prescribed sampling volume 313 is subsequently enclosed in the hollow lance 310. The sampling volume 313 is preferably chosen such that the withdrawn amount of finely divided solid material is sufficient for all the individual analyses intended, in order to avoid another sampling process from the same sampling jar.

A substantially circular cross section of the basic body 311 and of the sleeve 312, as in the example above, is advantageous from a production engineering viewpoint. According to the invention, however, other cross-sectional forms are also suitable, such as an ellipse, rectangle, hexagon or octagon. The basic body 311 and the sleeve 312 must merely enclose a suitable sampling volume 313 in the closed state. The two elements may be produced from the same material or from different materials, for example from metals such as aluminum or steel, but also from plastic, ceramic or glass.

In the hollow lance described above, the enclosing of the sample material in the sampling volume 313 takes place by the sleeve moving in the longitudinal direction over the basic body. FIG. 2c shows an alternative embodiment of a sampling means according to the invention, in which the enclosing of the sample material takes place by a rotating movement of the sleeve 312 in relation to the basic body 311. The sleeve 312 has an opening, which extends at most over half the circumference. The portion of reduced cross section of the basic body 311 is in this case not formed so as to run all the way round in the circumferential direction, but as a depression on one side, which can be completely covered by the continuous region of the sleeve 312, in order to form a sampling volume 313. The withdrawal of finely divided solid material takes place in a way analogous to the procedure described above.

Depending on the properties of the dosed solids, it may be necessary to clean part of the sampling means after a sampling operation, for example of adhering solids, in order to avoid contamination of a subsequent sample. An advantageous embodiment provides that for this purpose the relevant parts of the sampling means are exposed to a pressurized gas, for example air or nitrogen. This can also be performed in different ways. On the one hand, in the case of a hollow lance 310 as the sampling means, the basic body 311 may be provided with bores, which open out into the region of reduced cross section and through which compressed air for example can flow out. On the other hand, the relevant parts of the sampling means may also be treated with compressed air from the outside, for example by a cleaning device being brought up to the sampling means with the aid of a manipulator. Such a cleaning device may comprise not only the pressurized gas supply but also an extractor for the mixture of gas and solid material produced by the cleaning. It may also comprise mechanical cleaning tools such as brushes.

As already stated above, some methods of analysis require the dosing of finely divided solids into testing jars with a high dosing accuracy. FIG. 3 shows a preferred embodiment of a dosing means 320 according to the invention. A dosing means housing 321 has an inlet 322 and an outlet 323 for finely divided solids. The part of the inlet 322 protruding from the housing 321 may be advantageously designed as a funnel. A dosing wheel 324 is provided inside the housing 321 as a central element of the dosing means 320. The running surface of the dosing wheel 324 encloses with an inner wall of the housing 321 a volume through which finely divided solids can be transported by the rotation of the dosing wheel 324 from the inlet 322 to the outlet 323. The distance between the lower end of the inlet 322 and the running surface of the dosing wheel preferably corresponds to 1.2 to 3 times the largest particle dimension. The diameter of the inlet 322 at the lower end preferably corresponds to 1.5 to 2.5, times the largest particle dimension. The running surface of the dosing wheel 324 is typically designed in the form of a channel, for example u-shaped or v-shaped. The running surface and the inner wall of the housing 321, which comes into contact with the finely divided solids, is typically smooth, preferably polished, in order to avoid adhesive attachment of the finely divided solids. The dosing wheel housing may have further inlets and outlets, for example in order to subject the inner space to compressed air and blow out or suck away remains of finely divided solids.

FIG. 3 also shows a testing jar 12, which is located on a base. In order to dose finely divided solids into the testing jar 12, preferably an amount of solids is inserted into the inlet 322 from a sampling means described above. For this purpose, the sampling means and the dosing means 320 are provided in the automated analyzer in such a way that they are movable in relation to one another. For example, with a sampling means fixed in place, the dosing means 320 can be moved between the sampling means and the testing jar 12, for example by a manipulator that is movable linearly in the x direction. It is also possible, however, for the dosing means 320 to be fixed in place if the sampling means can be moved between the sampling jar 11 and the dosing means 320. The flexibility is increased if both the sampling means and the dosing means 320 are provided in such a way that they are movable.

While solid material pours out of the dosing means 320 into a testing jar 12, the mass of dosed solid material is registered by a weighing device and used for the purpose of controlling the dosing means 320. In the case of a dosing wheel 324 as an essential component part of the dosing means 320, the rotational speed, and consequently the circumferential speed, of the dosing wheel 324 can be controlled in accordance with the dosed amount. At the beginning of the dosing, the wheel may turn more quickly, and thereby feed in more dosed solid material. As the total mass of the solid material in the testing jar 12 approaches the desired value, the wheel turns more slowly, until it finally comes to a complete standstill and no more solid material is dosed. The weighing devices and the control system are in this case selected and designed in such a way that dosing accuracies of 0.1 g to 0.001 g can be ensured.

In order to achieve the most uniform possible distribution of the finely divided solids in a testing jar 12, the testing jar 12 or the base on which the testing jar 12 is located may, for example, be moved in an x-z direction during the dosing operation, for example linearly, circularly, elliptically, in the form of an eight or in some other prescribed manner. Uniform distribution is to be understood both in the sense of the same filling height at every point in the testing jar and with regard to the characteristics of the solid material, for example the grain size distribution.

In a further embodiment, firstly a prescribed amount of finely divided solids is dosed into a testing jar 12. Subsequently, the dosed amount is distributed as uniformly as possible, for example by movements of the testing jar 12 or with the aid of a stirrer.

EXAMPLE

An automated analyzer according to the invention and an automatic method of analysis according to the invention were used to monitor the product quality of water-absorbing polymers. In this case, 2 samples every hour were respectively subjected to the following method of analysis:

Absorption against Pressure (AAP)
Saline Flow Conductivity (SFC)
Free Swelling Rate (FSR)

The arrangement of the elements of the automated analyzer 1 corresponds to that represented in FIG. 1a. Samples were thoroughly mixed manually and placed in cylindrical sampling jars 11 with a diameter of 90 mm, a height of 160 mm and a filled amount of approximately 1000 cm$^3$ into a rack as a depot 10. To allow the analysis results to be assigned to the respective samples, the sampling jars 11 were provided with a barcode, which was manually registered during the placement of the sampling jars 11.

A manipulator 20, movable in three spatial directions x, y and z, moved the sampling jars 11 out of the depot 10 to the dosing device 30 and, after withdrawal of a sample, back again. A hollow lance 310 according to FIG. 2a and FIG. 2b was used as the sampling means; approximately 10 g of the finely divided solid material were withdrawn. The sampling means was fixed in place in the automated analyzer in the x and z directions, but could be moved in the y direction. A device with a dosing wheel 324 according to FIG. 3, which was movable in the x direction, was used as the dosing means 320. After the withdrawal of a sample from the sampling jar 11, the sampling jar 11 was placed back in the depot 10 by the manipulator 20. The dosing means 320 was subsequently brought into a position under the sampling means such that it emptied its content into the funnel of the dosing means 320 by opening of the hollow lance 310. To carry out the individual analyses, various amounts of finely divided solids were dosed into different testing jars 12.

Absorption Against Pressure (AAP)

The absorption under a pressure of 21.0 g/cm$^2$ (AUL0.3 psi) was determined according to the test method recommended by the EDANA, No. WSP 242.2-05 "Absorption under Pressure". It corresponds to ISO Standard 17190-7: 2001.

The absorption under a pressure of 49.2 g/cm$^2$ (AUL0.7 psi) was determined in a way analogous to the test method recommended by the EDANA, No. WSP 242.2-05 "Absorption under Pressure", a pressure of 49.2 g/cm$^2$ (AUL0.7 psi) being set instead of a pressure of 21.0 g/cm$^2$ (AUL0.3 psi).

The EDANA test method is obtainable, for example, from the publishing institution: EDANA, Avenue Eugène Plasky 157, B-1030 Brussels, Belgium.

For this method, a Plexiglas cylindrical measuring cell with an inside diameter of 60 mm and a height of 50 mm was used as the testing jar 12 provided in the depot 10. A full-face ram with a weight of 368 g was located in the empty measuring cell. For dosing, the measuring cell was placed by the manipulator 20 onto a plate on a balance of the type Sartorius LP620S, the ram removed and the dosing means 320 brought into a position over the measuring cell. 0.9 g of finely divided solids were dosed into the measuring cell with an accuracy of 0.005 g, the plate being moved in the x-z direction in the form of an eight, in order to provide a uniform distribution of the particles of solid material in the measuring cell. The ram was subsequently placed back in the measuring cell.

After the dosing, the measuring cell was transported by the manipulator 20 into the depot and deposited there on a glass filter plate covered with a filter paper in a Petri dish with a diameter of 200 mm and a height of 30 mm. 0.9% by weight of sodium chloride solution was introduced into the Petri dish by way of lines in the gripper 24 of the manipulator 20 until the liquid level reached the upper edge of the glass filter plate. The reaching of the desired filling level was ensured by means of contact electrodes in the gripper 24 of the manipulator 20.

After a swelling time of 60 minutes, the measuring cell was removed by the manipulator 20 from the depot 10 and placed on a balance. The current weight after liquid absorption and the original weight after dosing were used to calculate the AAP value, which was stored for this sample. Subsequently, the measuring cell was placed back in the depot 10.

Saline Flow Conductivity (SFC)

The method of analysis of SFC determination provides findings on the capability of a hydrogel layer to pass on liquid under a given pressure and a description of it can be found, for example, in the U.S. Pat. No. 5,599,335. The first method steps correspond to those of the AAP determination described above. However, a full-face ram was not used, but a ram with bores, as represented for example in FIGS. 7 to 9 of U.S. Pat. No. 5,599,335. The dosing accuracy was 0.001 g when dosing solid material of the 0.9 g.

Once the swelling time of 60 minutes had elapsed, the measuring cell was removed from the depot 10 by the manipulator 20 and transported onto a holding device, under which a jar stood on a balance. The height of the gel bed was determined by means of a laser and stored for later evaluation. Two litres of a 0.9% by weight sodium chloride solution were kept in a liquid reservoir. An outlet of the reservoir was moved over the measuring cell and the outlet valve opened, so that the liquid ran through the measuring cell into the jar located under it. It was ensured by appropriate arrangement of the reservoir and the outlet in relation to the position of the measuring cell that a liquid filling level of 50 mm was obtained in the measuring cell on account of the principle of communicating tubes. This filling level was maintained for a period of 10 minutes, the throughflow being measured and stored at intervals of 20 seconds. The throughflow was in this case determined with the aid of the balance on which the jar receiving the liquid running out of the measuring cell was standing. After completion of the analysis, these data were used to calculate the SFC value, which was stored for this sample. The measuring cell was placed back in the depot 10 by the manipulator 20.

Free Swelling Rate (FSR)

To determine the free swelling rate, a beaker with an inside diameter of 30 mm and a height of 50 mm was used as the testing jar 12, which was likewise provided in the depot 10. The dosing of the finely divided solid material proceeded in a way analogous to the method described above for the AAP and SFC determination, with the difference that 1 g of the particles was dosed with an accuracy of 0.1 g. After the dosing of solid material, the beaker was placed by the manipulator 20 on a balance, over which a light source and a CCD camera were located at a distance of approximately 40 cm. By means of a pump, 20 ml of 0.9% by weight sodium chloride solution were dosed into the beaker via a liquid line and the time it took for the entire liquid to be absorbed by the polymer particles was measured. Serving as a criterion for this was the change in the reflection of the light on the liquid surface, which was recorded by the CCD camera as a change in the gray scale value. The amount of dosed solid material, the dosed amount of liquid and the measured time period were used to calculate the FSR value, which was stored for the respective sample.

The stored information on the sample was compiled in a data record and stored in a laboratory data information system (LIMS) for documentation. By optimum coordination of the time periods required for the preparation for the analysis, for carrying out the analysis and for the evaluation of the analysis, it was possible to achieve a reduction in the overall duration in comparison with when the analysis are carried out manually. The automation allowed the reproducibility and reliability of the analysis to be increased.

The invention claimed is:

1. A method for automatic analysis of finely divided solids, comprising:
    moving, with a programmable manipulator, a sampling jar and a testing jar between a depot, a dosing station, and an analysis station,
    withdrawing a representative sample of the finely divided solids from the sampling jar and inserting a representative amount of the sample uniformly into the testing jar with a dosing accuracy of at least 0.1 g,
    dosing liquid into the testing jar,
    analyzing the sample in a standardized analysis, thereby obtaining analysis results, and
    making the analysis results available for further electronic processing.

2. The method of claim 1, wherein
    the finely divided solids comprise a water-absorbing polymer and
    said analyzing comprises at least one method selected from the group consisting of:
    Absorption against Pressure (AAP),
    Saline Flow Conductivity (SFC), and
    Free Swelling Rate (FSR).

3. The method of claim 1, wherein the dosing accuracy is at least 0.001 g.

4. The method of claim 1, wherein said withdrawing is carried out via a hollow lance.

5. The method of claim 4, wherein said inserting is carried out via a dosing device comprising a dosing wheel.

6. The method of claim 1, wherein said inserting is carried out via a dosing device comprising a dosing wheel.

7. The method of claim 6, wherein a rotational speed of the dosing wheel is controlled to achieve the dosing accuracy.

8. A method for automatic analysis of finely divided solids, comprising:
    moving, with a programmable manipulator, a sampling jar and a testing jar between a depot, a dosing station, and an analysis station,
    withdrawing a representative sample of the finely divided solids from the sampling jar via a sampling device and inserting a representative amount of the sample uniformly into the testing jar with a dosing accuracy of at least 0.1 g via a dosing device,
    dosing liquid into the testing jar,
    analyzing the sample in a standardized analysis, thereby obtaining analysis results, and
    making the analysis results available for further electronic processing,
    wherein
    the automatic analysis is carried out in an automated analyzing system comprising:
    the depot for the sampling jar and the testing jar,
    an analysis device for said analyzing,
    the programmable manipulator,
    a solids dosing device comprising the sampling device and the dosing device, and
    a liquids dosing device.

9. The method of claim 8, wherein
    the finely divided solids comprise a water-absorbing polymer and
    said analyzing comprises at least one method selected from the group consisting of:
    Absorption against Pressure (AAP),
    Saline Flow Conductivity (SFC), and
    Free Swelling Rate (FSR).

10. The method of claim 8, wherein the dosing accuracy is at least 0.001 g.

11. The method of claim 8, wherein the sampling device is a hollow lance.

12. The method of claim 11, wherein the dosing device comprises a dosing wheel.

13. The method of claim 8, wherein the dosing device comprises a dosing wheel.

14. The method of claim 13, wherein a rotational speed of the dosing wheel is controlled to achieve the dosing accuracy.

* * * * *